US009789258B2

(12) United States Patent
Holtwick et al.

(10) Patent No.: US 9,789,258 B2
(45) Date of Patent: Oct. 17, 2017

(54) DOSE SETTING MECHANISM FOR A DRUG DELIVERY DEVICE

(71) Applicant: SANOFI-AVENTIS DEUTSCHLAND GMBH, Frankfurt am Main (DE)

(72) Inventors: Marc Holtwick, Frankfurt am Main (DE); Michael Jugl, Frankfurt am Main (DE); Axel Teucher, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 183 days.

(21) Appl. No.: 14/435,797

(22) PCT Filed: Nov. 5, 2013

(86) PCT No.: PCT/EP2013/073077
§ 371 (c)(1),
(2) Date: Apr. 15, 2015

(87) PCT Pub. No.: WO2014/072298
PCT Pub. Date: May 15, 2014

(65) Prior Publication Data
US 2015/0265771 A1  Sep. 24, 2015

(30) Foreign Application Priority Data
Nov. 8, 2012 (EP) .................................. 12191749

(51) Int. Cl.
*A61M 5/315*  (2006.01)
*A61M 5/20*  (2006.01)

(52) U.S. Cl.
CPC ............ *A61M 5/3155* (2013.01); *A61M 5/20* (2013.01); *A61M 5/31583* (2013.01);
(Continued)

(58) Field of Classification Search
CPC .. A61M 5/3155; A61M 5/20; A61M 2205/42; A61M 2205/581; A61M 5/31583
See application file for complete search history.

(56) References Cited

U.S. PATENT DOCUMENTS

2011/0054412 A1  3/2011  Eich et al.
2012/0136317 A1*  5/2012  Teucher ............ A61M 5/31555
                                              604/208
(Continued)

FOREIGN PATENT DOCUMENTS

EP      2060288      5/2009
WO      88/08725     11/1988
(Continued)

OTHER PUBLICATIONS

European Search Report for EP App. No. 12191749, dated Jul. 3, 2013.
(Continued)

*Primary Examiner* — Bradley Osinski
(74) *Attorney, Agent, or Firm* — McDonnell Boehnen Hulbert & Berghoff LLP

(57) ABSTRACT

The present invention is directed at a dose setting mechanism for a drug delivery device, comprising an outer sleeve and an inner sleeve located at least partially within the outer sleeve wherein the outer sleeve is connected to the inner sleeve. To reduce noise excitations of the dose setting mechanism, at least one intermediate element is at least partially located in a clearance between the inner sleeve and the outer sleeve in such way that it reduces the relative movement of the inner sleeve and the outer sleeve along a play between the inner sleeve and the outer sleeve. The invention is further directed to a pen-type injector equipped with a respective dose setting mechanism.

13 Claims, 3 Drawing Sheets

(52) U.S. Cl.
CPC ... *A61M 2205/42* (2013.01); *A61M 2205/581* (2013.01); *A61M 2205/583* (2013.01)

(56) References Cited

U.S. PATENT DOCUMENTS

| 2013/0211331 | A1* | 8/2013 | Smith | A61M 5/31555 |
| | | | | 604/151 |
| 2015/0148750 | A1* | 5/2015 | Pedersen | A61M 5/20 |
| | | | | 604/207 |

FOREIGN PATENT DOCUMENTS

| WO | 2011/068531 | 6/2011 |
| WO | 2011/154483 | 12/2011 |
| WO | 2013/098194 | 7/2013 |

OTHER PUBLICATIONS

International Search Report and Written Opinion for Int. App. No. PCT/EP2013/073077, dated Feb. 7, 2014.

\* cited by examiner

DOSE SETTING MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2013/073077 filed Nov. 5, 2013, which claims priority to European Patent Application No. 12191749.6 filed Nov. 8, 2012. The entire disclosure contents of these applications are herewith incorporated by reference into the present application.

TECHNICAL FIELD

The present invention is directed at dose setting mechanism for a drug delivery device comprising an outer sleeve and an inner sleeve located at least partially within the outer sleeve, wherein the outer sleeve is connected to the inner sleeve. The invention is also directed at a pen-type injector equipped with a respective dose setting mechanism.

BACKGROUND

Pen type drug delivery devices have applications where regular injection by persons without formal medical training occurs. This is increasingly common among patients having diabetes or the like. Self-treatment enables such patients to conduct effective management of their disease. The injection pens usually comprise a housing in which a drive mechanism is located. Some kinds of drug delivery devices also comprise a compartment to accommodate a cartridge in which the medicament is received. By means of the drive mechanism, a bung in the cartridge is displaced such that the medicament accommodated therein is dispensed normally through a needle.

Prior to injection, the required dose of the medicament is set by means of a dose setting mechanism. Common designs of dose setting mechanisms comprise a number of tubular or sleeve-like elements such as a dose dial sleeve, a number or dose indicating sleeve, a drive sleeve or a ratchet sleeve that extends in a longitudinal direction from a proximal end to a distal (injecting) end of the drug delivery device. Such sleeves are often accommodated within and connected to each other.

One alternative of dose setting mechanism includes a dose selector or dose dial element that charges a torsion spring by rotation, wherein one end of this spring is rotationally fixed to the dose selector. For an audible signal during dose setting, a ratchet sleeve is connected with the dose selector and is rotated in a first direction. For dose cancellation or dose reduction, the ratchet sleeve is rotated in the opposite direction. During dose setting or dose cancellation, the ratchet produces an audible and tactile click sound by flexible arms of the ratchet snapping over corresponding counterparts located in or at the housing, e.g. ratchet teeth, which is detectable by the human ear. The flexible arm and the corresponding counterpart are called ratchet element in the following. However, the sound produced is in some cases experienced as unpleasant for the user and is interpreted as improper functioning of the device.

In document WO 2011/068531 A1, a leadscrew is rotationally restrained in a passage of a driver. The driver has flexible legs to reduce play between mating cross sections of the leadscrew and the passage to improve dose accuracy. The flexible legs are exclusively provided for guiding the lead screw. A leadscrew brake accommodates the leadscrew such that relative rotation is prevented. A ratchet mechanism between the leadscrew and the body produces a click-sound during dose delivery. By rotation of a dose set knob, the dose set knob screws out of the housing and carries a setback element in the same direction with a ratchet located therebetween, which produces a click-sound during dose setting. The setback element is rotationally fixed to a driver which is moved axially by stop member relative to the leadscrew but does not rotate. Vibrations that emerge from the dose setting mechanism during dose setting produce uncomfortable chatter sound when there is play between the setback element and the driver.

In the injection device described in US 2011/0054412 A1, a traveler is provided between a coupling sleeve and a threaded sleeve and engages the threaded sleeve via a thread. A ratchet is provided between the housing and a dose setting button. The housing surrounds the threaded sleeve, wherein the threaded sleeve may rotate relative to the housing. The traveler interconnects the coupling sleeve and the threaded sleeve and due to the thread engagement, the traveler and threaded sleeve can rotate relative to each other. None of the threaded sleeve or the coupling sleeve has a ratchet element or is directly connected to a ratchet element so that vibration excitations resulting from the ratchet are not directly induced into one of the components.

In EP 2 060 288 A1, a spring is arranged between an outer control element and an item, in which the spring is retained. The spring is arranged such as to be elastically deformed when the control element is rotated relative to the outer control element and has three salients which provide stable and defined positions of the control element. Rotation of the outer control element relative to the item is essential to create a restoring force.

The drive assembly described in WO 2011/154483 A1 comprises a sleeve arrangement with a housing part, a first and a second drive part located therebetween. An elastic spring provides a separating force acting on the drive parts. The spring is part of a uni-directional clutch mechanism, which only acts in axial direction. The coupling members are arranged such that the produce a click-sound. Vibrations can directly be induced into inner sleeve arrangement as the spring provides no compensation.

In WO 88/08725 A1 an elastic sealing ring is provided between the left end of an outer housing and an attachment sleeve serving as a sliding coupling. The attachment sleeve is fixedly connected to a ratchet with a ratchet arm, which interacts with recesses on the outer surface of an adjusting sleeve. Principally, the elastic sealing ring may absorb vibrations, but it is outside a vibration transmission path that runs through the dose setting mechanism.

SUMMARY

It is an object of the invention to reduce the sound feedback in such a dose setting mechanism.

The above problem is solved by a dose setting mechanism as defined in claim 1 and a drug delivery device as defined in claim 13. In particular, at least one intermediate element is at least partially located in a clearance between the inner sleeve and the outer sleeve in such way that it reduces the relative movement of the inner sleeve and the outer sleeve along a play between the inner sleeve and the outer sleeve.

During dose setting or dose cancelling, the snapping action of the ratchet arms of the ratchet sleeve (inner sleeve) produces the click sound. The inventors now found out that the ratchet sleeve and another sleeve, in particular an outer sleeve, that is rotationally fixed to the ratchet sleeve, e.g. by a groove or spline connection or the like, show a degree of play between each other due to tolerance variations. The play can be characterized as a degree of free space between mating components or as a production-related freedom of movement in which a component can move relatively to its mating component after assembly. The play occurs e.g. in radial direction so that the longitudinal axes of the sleeves may shift or tilt relatively to each other. It can also occur in circumferential direction e.g. in the groove or spline connection such that the sleeves may rotate relative to each other over a small angle. During investigations of this play the inventors arrived at the conclusion that the play is responsible for the unpleasant sound generated by the dose setting mechanism. The vibration excitations resulting from the ratchet are induced into the ratchet sleeve. As to the fact that the outer sleeve surrounds the ratchet sleeve in a tube-like manner, play between the components results in an uncomfortable chatter sound when the two components abut each other. Further, the outer sleeve is stimulated into vibrations as well and produces an intense feedback sound. The sound may be even more intense when different teething angles on the ratchet are provided. Different ramp angles influence the frequency and/or amplitude of the excitation depending on the rotation direction. Ratchets often comprise angled teeth that have ramp angles that are different depending on the rotation direction. For example, the ramp surface that engages a counterpart in the housing during dose dialing is aligned under a more flat angle with respect to the longitudinal axis of the drug delivery device than the ramp surface for dose cancelling.

By providing at least one intermediate element at least partially in a clearance between the inner sleeve and the outer sleeve, a relative movement of the inner sleeve and the outer sleeve along a play is minimized and the sound transfer and sound amplification is effectively reduced. Preferably, the inner sleeve is a ratchet sleeve, i.e. a sleeve that comprises ratchet elements, alternatively, the outer sleeve is a ratchet sleeve. Vibration excitations are effectively damped. In a preferred embodiment, it has been proven effective when the intermediate element interconnects the ratchet sleeve and a number sleeve, with the number sleeve constituting the outer sleeve.

To enhance the vibration characteristic of the drug delivery device, the intermediate element may be elastically deformable and resiliently interconnects the outer sleeve and the inner sleeve. Accordingly, tolerance and play deviations may be compensated by the intermediate element effectively. This is particularly beneficial as the play between the inner sleeve and the outer sleeve may vary in longitudinal direction because of production related factors. The vibrations and sound producing characteristics of the sleeve arrangement of the outer and inner sleeve is less tolerance sensitive.

In the sense of the invention, either the inner sleeve or the outer sleeve can be excited to vibrations, wherein in each case the intermediate position of the intermediate element provides for effective damping. In such inner and outer sleeve arrangements, it has been proven effective when the vibration absorption is conducted as close to the source of the vibrations as possible.

It is possible that the inner ratchet sleeve directly comprises a ratchet element or is connected to a ratchet element such that the vibrations are directly induced into the inner ratchet sleeve. Similarly, the outer ratchet sleeve may directly comprise a ratchet element or may be connected to a ratchet element such that the vibrations are directly induced into the outer ratchet sleeve.

The dose setting mechanism for a drug delivery device may comprise an inner ratchet sleeve located at least partially within an outer sleeve, wherein the inner ratchet sleeve and the outer sleeve are rotationally fixed to each other. During dose setting or dose cancellation, vibration excitations resulting from a ratchet element of the inner ratchet sleeve are directly induced into the inner ratchet sleeve. At least one elastically deformable intermediate element is at least partially located in a clearance between the inner ratchet sleeve and the outer sleeve and resiliently interconnects the inner ratchet sleeve and the outer sleeve and reduces a radial and/or a rotational play between the inner ratchet sleeve and the outer sleeve in such way that the vibrations excitations are damped.

The technical mode of action is also achieved by a dose setting mechanism for a drug delivery device, comprising an inner sleeve located at least partially within an outer ratchet sleeve, the inner sleeve and the outer ratchet sleeve being rotationally fixed to each other. During dose setting or dose cancellation, vibration excitations resulting from a ratchet element of the outer ratchet sleeve are directly induced into the outer ratchet sleeve. At least one elastically deformable intermediate element is at least partially located in a clearance between the inner sleeve and the outer ratchet sleeve and resiliently interconnects the inner sleeve and the outer ratchet sleeve and reduces a radial and/or a rotational play between the inner sleeve and the outer ratchet sleeve in such way that the vibrations excitations are damped.

A major advantage of the intermediate element is that it constantly interconnects the inner sleeve and the outer sleeve so that the intermediate element is always in contact with both of the sleeves. Deviations in the relative position between the inner sleeve and the outer sleeve may be compensated by the elastically deformable properties of the intermediate element. Accordingly, the intermediate element provides for efficient damping characteristics when the play between the inner sleeve and the outer sleeve decreases or increases.

Preferably, the intermediate element has damping properties and may be configured such that it absorbs a significant proportion of the vibrations of the sleeves.

According to a further embodiment, the intermediate element is a crush element. The intermediate element may be installed between the inner sleeve and the outer sleeve in a pre-stressed manner. In other words, the crush element is compressed and deformed during assembly of the sleeve arrangement. In a further embodiment of the invention, the crush element is once plastically deformed by the outer surface of the inner sleeve and the inner surface of the outer sleeve during the assembly of the parts.

The intermediate element may be attached to one of the inner sleeve and the outer sleeve. It can either be attached to the inner surface of the outer sleeve or to the outer surface of the inner sleeve.

According to a further embodiment, the intermediate element has a higher elasticity than the inner sleeve and/or the outer sleeve. Preferably, the intermediate element and the respective sleeve are made of different materials. According to a further embodiment, the intermediate element is formed by two shot molding (2K molding). Two shot molding includes a two-step process molding with different plastic compounds. It has been proven effective when the intermediate element comprises a thermoplastic elastomer. Due to the fact that thermoplastic elastomers show advantages typical of both rubbery materials and plastic materials, it is well suitable for vibrations damping and oscillation absorption.

It is also possible to provide the element with the same material as the respective sleeve. Accordingly, the element may be integrally formed with the respective sleeve which is cost effective during manufacturing.

According to a further embodiment of the present invention, the intermediate element is formed as a rib. The rib may be of elongated shape and may be configured such that it extends in a longitudinal direction of the drug delivery device.

In order to enhance the sound characteristics of the dose setting mechanism, a plurality of intermediate elements can be distributed around the periphery of at least a section of the inner sleeve. For example, a plurality of parallel ribs that extend in the longitudinal direction can be spaced at regular or irregular intervals over the outer circumference of the inner sleeve. Preferably, the intermediate elements are equally distributed around the inner sleeve in a symmetric manner.

According to another preferred embodiment of the invention, the intermediate element has a triangular cross section in longitudinal direction. Preferably, an apex of the triangle projects from the surface of the inner or the outer sleeve in a radial direction. Thereby, not only friction between the elements can be reduced but also effective vibration damping characteristics can be achieved. Other cross-sectional shapes are possible as well, for example a round or an elliptical or an oval cross-section.

The object of the present invention is further achieved by a pen-type injector, having a housing and a cartridge holder containing a medical product such as a medicament and a dose setting mechanism as described above.

In particular, the advantages of the present invention make a positive difference when the pen-type injector is a disposable injection device. Such devices can be thrown away or recycled after the content of the medicament has been exhausted. However, the present invention is also applicable with re-usable devices designed to replace an empty cartridge with a filled one after the whole content of the former cartridge has been administered.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2, H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention will be described by way of examples and with reference to the schematic drawings in which.

DETAILED DESCRIPTION

Figure 1:
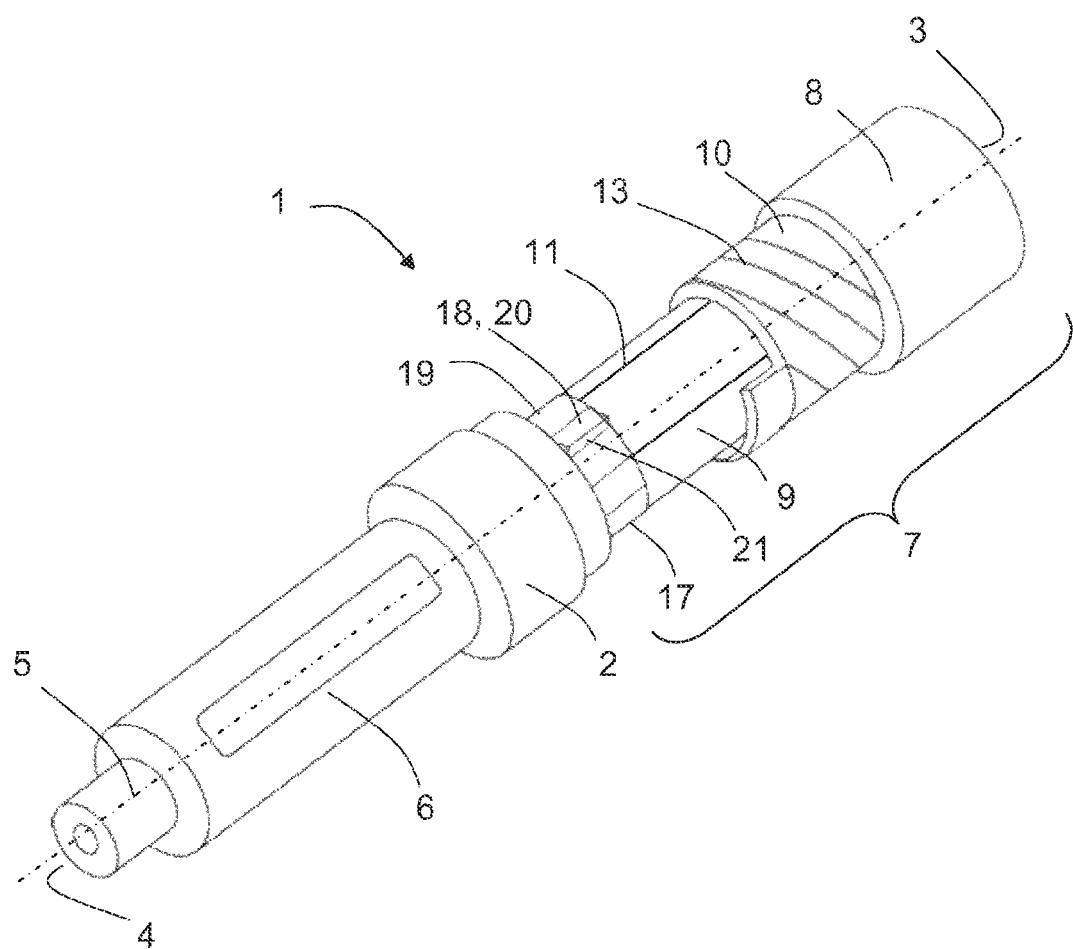
FIG. 1 shows a perspective view of an inventive drug delivery device with a part of the inventive dose setting mechanism.

FIG. 1 shows a disposable drug delivery 1 device with a housing 2 having a proximal end 3 and a distal end 4 and a longitudinal axis 5. At the distal end 4 of the drug delivery device 1 a cartridge holder 6 is located containing a cartridge with a medicinal product for example a medicament such as insulin. A section of the housing 2 extending from a center section of the drug delivery in proximal direction is partially cut open to expose elements of an inventive dose setting mechanism 7.

At the proximal end 3, the dose setting mechanism 7 comprises a dose dial element 8, resp. a dose selector or a dose dial grip. A ratchet sleeve 9 forming the inner sleeve is located within a number sleeve 10, the number sleeve 10 constituting an outer sleeve that partially surrounds ratchet sleeve 9. The number sleeve 10 is provided on its outer surface with a number of indices (not shown) indicating the set dose. The ratchet sleeve 9 is connected to a spring (not shown) to generate the driving forces for a drive mechanism (not shown).

Figure 2:
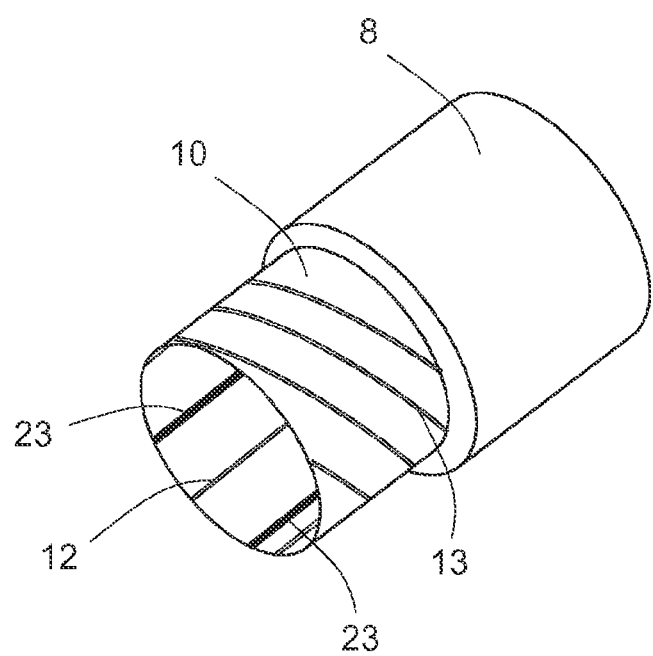
FIG. 2 shows a perspective view of another part of the dose setting mechanism of FIG. 1.

The ratchet sleeve 9 surrounds a drive shaft (not shown) of the drive mechanism and is connected to the drive shaft via a snap connection, thus being rotationally and axially fixed with respect drive shaft. The dose dial element 8 is rotationally coupled to the ratchet sleeve 9 via the drive shaft, wherein the drive shaft is rotationally coupled to the dose dial element 8 via a clutch element such that when the dose dial element 8 is rotated in a first direction, the ratchet sleeve 9 rotates in unison. The number sleeve 10 is rotationally coupled to the ratchet sleeve 9 by way of a spline connection with the ratchet sleeve 9 having a plurality of longitudinally extending splines 11 (see FIG. 1) and the number sleeve 10 having a plurality of longitudinally extending grooves 12 (see FIG. 2). The number sleeve 10 is provided with an outer helical thread 13 engaging a corresponding projection on the inner surface of the housing 2 such that upon rotation of the number sleeve 10, it rotates and moves axially with respect to the housing 2.

The ratchet sleeve 9 and the number sleeve 10 are arranged such that there is a clearance or gap 14 (see FIG. 3) between an inner surface 15 of the number sleeve 10 and an outer surface 16 of the ratchet sleeve 9. At a distal end, the ratchet sleeve 9 is provided with a ratchet mechanism 17. The ratchet mechanism 17 comprises a number of ratchet arms 19, each with a ramp 18.

For dose dialing, the dose dial element 8 is rotated in a first direction (e.g. clockwise direction) forcing the ratchet sleeve 9 to rotate in the same. When the ratchet sleeve 9 rotates, each ramp 18 of the ratchet mechanism 17 interacts with ratchet teeth on a locking nut (not shown), which is located in the housing 2 and which is prevented from rotation relative to the housing 2 by external ribs engaging teeth in the housing 2. As the ratchet arms 19 run over the ratchet teeth of the locking nut, an audible and tactile click sound is produced which indicates the user that a unit of the dose is set. By rotating the ratchet sleeve 9, the number sleeve 10 moves axially with respect to the ratchet sleeve 9 and the housing 2 due to the spline connection between the ratchet sleeve 9 and the number sleeve 10 and the helical thread connection between the number sleeve 10 and the housing 2. During dose dialing, rotation of the ratchet sleeve 9 causes the spring (not shown) to wound in torsion, wherein the ratchet mechanism 17 prevents the spring from rewinding in the opposite direction. For cancelling a dose, the ratchet sleeve 10 is rotated in the opposite direction (cf. counter-clockwise direction) by rotation of the dose dial element 8 in the same.

For dose dispensing, the user presses a dose button (not shown) at the proximal end of the drug delivery device 1, the dose button being connected to the clutch element such that movement of the dose button in distal direction causes the clutch to disengage such that the drive shaft is free to rotate relative to the dose dial element 8. Forward movement of the dose button also causes distal movement of the drive sleeve and the ratchet sleeve 9 thereby disengaging the locking nut from housing, the locking nut then being free to rotate and the stored energy of the spring to be released, thereby causing to ratchet sleeve 9 and the number sleeve 10 to rotate in the opposite direction. Rotation of the locking nut also causes a piston rod (not shown) to rotate and to advance in distal direction thereby causing dispense of the medicament in the cartridge in a way known to the skilled person.

During dose setting and dose cancellation, the ramp 18 of the ratchet mechanism 17 produces a click sound and induces vibrations into the number sleeve 10. When dialing a dose, a first ramp surface 20 is responsible for the click sound, wherein during dose cancellation, a second ramp surface 21 located opposite the first ramp surface 20 and formed steeper than the first ramp surface 20 is responsible for a sound that indicates the reduced dose unit.

Figure 3:
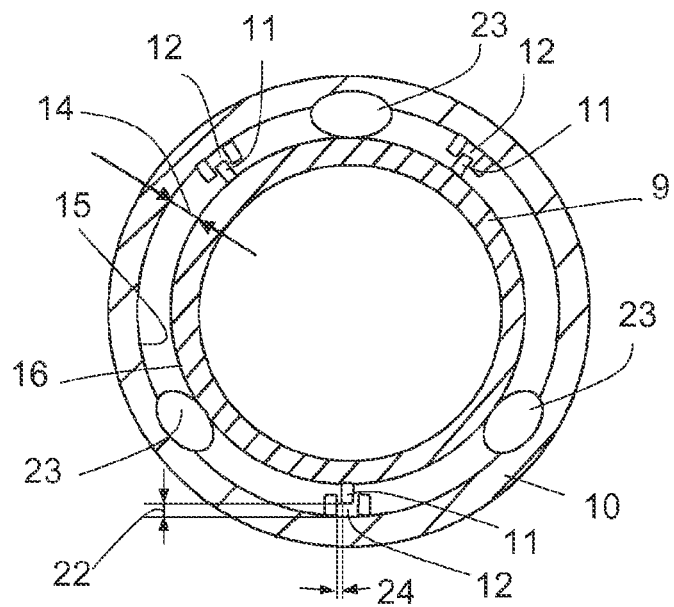
FIG. 3 shows a cross-sectional view of the drug delivery device of FIG. 1.

As illustrated in FIG. 3, a radial play 22 is provided due to manufacturing inaccuracies in which relative radial movement between the components 9, 10 is initially possible. Due to the axial length of the ratchet sleeve 9 and the number sleeve 10, the radial play 22 may vary in axial direction of the sleeves. Further, a rotational play 24 is provided, in which relative rotational movement between the components 9, 10 is initially possible. To minimize the possible relative radial or rotational movement, the number sleeve 10 is provided with a number of crush ribs 23 on its inner surface 15, which extend in a longitudinal direction parallel to the longitudinal axis 5 of the drug delivery device 1 (see FIG. 2). The crush ribs 23 are arranged in such way that they are distributed around the inner periphery of the number sleeve 10 in a rotationally symmetric matter (see FIG. 3).

The crush ribs 23 are made of thermoplastic elastomer, are molded on the number sleeve 10 in a two-step molding process and are attached to the number sleeve 10 herewith. The crush ribs 23 have an oval cross-section with a circumferential inner section of the crush ribs 23 contacting the outer surface 16 of the ratchet sleeve 9 wherein the crush ribs 23 have been compressed in radial direction when the ratchet sleeve 9 was installed within the number sleeve 10. FIG. 3 shows the crush ribs 23 in a pre-stressed state. When vibrations are induced into the ratchet sleeve 9, the ratchet sleeve 9 is forced to vibrate. As the crush ribs 23 are closely connected to each other and are preferably able to deform elastically, the relative movement between the ratchet sleeve 9 and the number sleeve 10 in radial or circumferential direction has to override a resistance and is thereby effectively reduced without the inner surface 15 of the number sleeve 10 making direct contact with the outer surface 16 of the ratchet sleeve 9. Thereby, vibrations are damped and absorbed and the sound that is produced during dose dialing and dose cancellation is effectively reduced.

Figure 4:
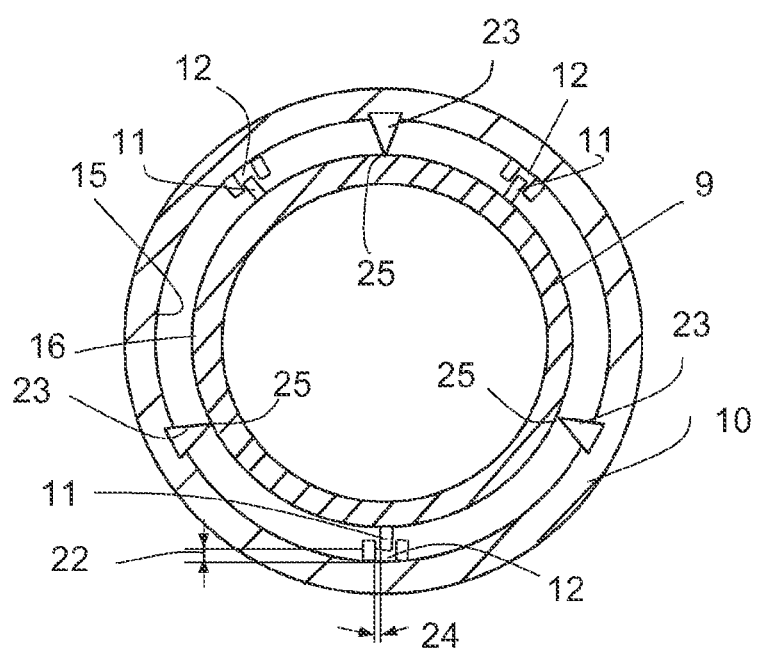
FIG. 4 shows a cross-sectional view of a dose setting mechanism in accordance with a second embodiment of the present invention.

The further embodiment shown in FIG. 4 differs from the design in FIG. 3 in the cross sectional shape of the crush ribs 23. The crush elements 23 in FIG. 4 have a triangular cross-section. The apex 25 of the triangle or one corner of the triangle, respectively, is directed towards the circle center of the number sleeve 10. The triangular shape minimizes the contact surface at the apex 25 with the ratchet sleeve 9 thereby effectively reducing friction during relative movement of the number sleeve 10 and the ratchet sleeve 9.

The invention claimed is:

1. Dose setting mechanism for a drug delivery device comprising:
    an inner ratchet sleeve located at least partially within an outer sleeve, the inner ratchet sleeve and the outer sleeve being rotationally fixed to each other during dose setting and dose cancellation, where vibration excitations resulting from a ratchet element of the inner ratchet sleeve are induced into the inner ratchet sleeve; and
    at least one elastically deformable intermediate element is located directly on a surface of one of the inner ratchet sleeve and the outer sleeve and is at least partially located in an annular clearance between the inner ratchet sleeve and the outer sleeve extending in a longitudinal direction along the surface parallel to a longitudinal axis of the drug delivery device,
    wherein the intermediate element deforms and resiliently interconnects the inner ratchet sleeve and the outer sleeve and reduces a radial and/or a rotational play between the inner ratchet sleeve and the outer sleeve in such way that the vibration excitations are damped.

2. Dose setting mechanism according to claim 1, characterized in that the intermediate element has damping properties.

3. Dose setting mechanism according to claim 1, characterized in that the intermediate element is a crush element.

4. Dose setting mechanism according to claim 1, characterized in that the intermediate element is attached to one of the inner ratchet sleeve and the outer sleeve.

5. Dose setting mechanism according to claim 1, characterized in that the intermediate element is formed by two shot molding.

6. Dose setting mechanism according to claim 1, characterized in that the intermediate element is made of thermoplastic elastomers.

7. Dose setting mechanism according to claim 1, characterized in that the intermediate element is of the same material as one of the sleeves.

8. Dose setting mechanism according to claim 1, characterized in that the intermediate element is formed as a rib.

9. Dose setting mechanism according to claim 1, characterized in that a plurality of intermediate elements is distributed around the periphery of at least a section of the inner sleeve.

10. Dose setting mechanism according to claim 1, characterized in that the intermediate element has a triangular cross-section.

11. Pen-type injector for delivering a medicament, including a dose setting mechanism according to claim 1.

12. Dose setting mechanism for a drug delivery device comprising:
    an inner sleeve located at least partially within an outer ratchet sleeve, the inner sleeve and the outer ratchet sleeve being rotationally fixed to each other during dose setting and cancellation, where vibration excitations resulting from a ratchet element of the outer ratchet sleeve are induced into the outer ratchet sleeve; and
    at least one elastically deformable intermediate element is located directly on a surface of one of the inner sleeve and the outer ratchet sleeve and is at least partially located in an annular clearance between the inner sleeve and the outer ratchet sleeve extending in a longitudinal direction along the surface parallel to the longitudinal axis of the drug delivery device,
    wherein the intermediate element deforms and resiliently interconnects the inner sleeve and the outer ratchet sleeve and reduces a radial and/or a rotational play between the inner sleeve and the outer ratchet sleeve in such way that the vibration excitations are damped.

13. Dose setting mechanism according to claim 12, characterized in that the intermediate element is attached to one of the inner sleeve and the outer ratchet sleeve.

* * * * *